(12) United States Patent
Hansen et al.

(10) Patent No.: US 12,380,292 B2
(45) Date of Patent: *Aug. 5, 2025

(54) METHOD OF UNLOCKING AN OPERATION OF A DEVICE WITH A TINY RFID TAG EMBEDDED ON AN INTEGRATED CIRCUIT

(71) Applicants: Scott Robert Hansen, Irvine, CA (US); Louisa Marie Hansen, Irvine, CA (US)

(72) Inventors: Scott Robert Hansen, Irvine, CA (US); Louisa Marie Hansen, Irvine, CA (US)

(73) Assignee: Viking Discoveries LLC, Irvine, CA (US)

( * ) Notice: Subject to any disclaimer, the term of this patent is extended or adjusted under 35 U.S.C. 154(b) by 180 days.

This patent is subject to a terminal disclaimer.

(21) Appl. No.: 18/133,415

(22) Filed: Apr. 11, 2023

(65) Prior Publication Data

US 2023/0289539 A1    Sep. 14, 2023

Related U.S. Application Data

(63) Continuation-in-part of application No. 17/968,783, filed on Oct. 18, 2022, now Pat. No. 11,626,206, and a continuation-in-part of application No. 17/567,011, filed on Dec. 31, 2021, now Pat. No. 11,475,993.

(51) Int. Cl.
| | |
|---|---|
| *H04Q 5/22* | (2006.01) |
| *G06F 21/62* | (2013.01) |
| *G06K 7/10* | (2006.01) |
| *G06K 19/07* | (2006.01) |

(52) U.S. Cl.
CPC ..... *G06K 7/10297* (2013.01); *G06F 21/6218* (2013.01); *G06K 19/0723* (2013.01)

(58) Field of Classification Search
CPC ............ G06K 7/10297; G06K 19/0723; G06F 21/6218
See application file for complete search history.

(56) References Cited

U.S. PATENT DOCUMENTS

| | | | | |
|---|---|---|---|---|
| 3,602,579 A | * | 8/1971 | Silvertooth | ............ G03B 27/73 355/36 |
| 5,956,048 A | * | 9/1999 | Gaston | ................ G06F 15/0283 361/679.01 |
| 6,851,822 B2 | * | 2/2005 | Herrera | ............... F21V 33/0048 362/802 |
| 6,885,288 B2 | * | 4/2005 | Pincus | .................. G01S 13/878 340/870.07 |

(Continued)

*Primary Examiner* — Quang Pham
(74) *Attorney, Agent, or Firm* — Scott R Hansen; Viking IP Law (57) ABSTRACT

A method includes reading data encoded on a tiny RFID tag that is embedded in an integrated circuit. The RFID tag has an area of 0.1 mm$^2$ or less and, alternatively, of 0.05 mm$^2$ or less. When the data satisfies predetermined criteria, a capability of a device or system is unlocked. The method may be used in conjunction with artificial intelligence (AI) for identification and authentication, fraud detection, behavioral analysis, predictive analytics, and/or access control, for example. The method may also be used in credit and/or debit card transactions, in which the tiny RFID tag and integrated circuit are on a credit and/or debit card. In another embodiment, the RFID tag and IC are incorporated into a label. The label may optionally be on a good for sale.

28 Claims, 9 Drawing Sheets

(56) References Cited

U.S. PATENT DOCUMENTS

| | | | | |
|---|---|---|---|---|
| 7,006,116 | B1* | 2/2006 | Meyers | G06F 21/62 713/184 |
| 7,065,557 | B2* | 6/2006 | Sowden | G06F 1/1656 709/227 |
| 7,780,618 | B2* | 8/2010 | Felt | A61M 37/00 210/90 |
| 7,901,834 | B2* | 3/2011 | Adams | H01M 8/04089 429/515 |
| 8,632,001 | B1* | 1/2014 | Ramachandran | G06Q 20/3227 235/375 |
| 9,188,976 | B1* | 11/2015 | Kim | G06Q 90/00 |
| 2002/0177330 | A1* | 11/2002 | Haffenden | H01R 13/6315 439/6 |
| 2003/0073326 | A1* | 4/2003 | MacLaren | H01R 13/64 439/43 |
| 2003/0135748 | A1* | 7/2003 | Yamada | H04M 1/675 713/193 |
| 2004/0180657 | A1* | 9/2004 | Yaqub | H04L 63/0853 455/411 |
| 2005/0026643 | A1* | 2/2005 | White | H04M 1/0256 455/575.1 |
| 2005/0085760 | A1* | 4/2005 | Ware | A61M 1/3451 604/4.01 |
| 2005/0198208 | A1* | 9/2005 | Nystrom | H04W 12/068 709/219 |
| 2005/0264540 | A1* | 12/2005 | Niwa | G06F 1/1647 345/173 |
| 2005/0277890 | A1* | 12/2005 | Stewart | G16H 20/17 235/375 |
| 2005/0280511 | A1* | 12/2005 | Yokoyama | G06K 19/0723 340/10.5 |
| 2006/0148454 | A1* | 7/2006 | Welch | H04M 1/7246 455/414.1 |
| 2006/0149727 | A1* | 7/2006 | Viitaharju | G06F 21/10 707/999.005 |
| 2007/0023516 | A1* | 2/2007 | Chapman | G06K 17/00 235/432 |
| 2008/0048837 | A1* | 2/2008 | Montgomery | G06K 19/0716 235/375 |
| 2008/0128492 | A1* | 6/2008 | Roth | G06Q 30/018 235/380 |
| 2008/0196170 | A1* | 8/2008 | Choi | D06F 34/18 68/12.02 |
| 2009/0134973 | A1* | 5/2009 | Sandler | G08B 21/0213 340/10.1 |
| 2009/0328203 | A1* | 12/2009 | Haas | G07C 9/33 726/20 |
| 2010/0052853 | A1* | 3/2010 | Hilton | G06F 21/32 340/5.82 |
| 2011/0029115 | A1* | 2/2011 | Ogawa | G09G 3/3611 700/117 |
| 2011/0231452 | A1* | 9/2011 | Nakajima | G06F 11/1469 707/E17.005 |
| 2012/0139693 | A1* | 6/2012 | Zucker | H04N 21/44008 340/5.2 |
| 2013/0208414 | A1* | 8/2013 | Moser | G06F 1/1626 361/679.32 |
| 2014/0122748 | A1* | 5/2014 | Pat | G06F 8/65 710/13 |
| 2014/0155951 | A1* | 6/2014 | Doerr | A61N 1/37211 607/9 |
| 2014/0323053 | A1* | 10/2014 | Yamaoka | H04M 1/72412 455/41.2 |
| 2015/0034716 | A1* | 2/2015 | Rouchouze | G02C 11/10 235/380 |
| 2015/0134552 | A1* | 5/2015 | Engels | G06Q 10/087 705/318 |
| 2015/0181410 | A1* | 6/2015 | Liu | H04W 12/04 455/419 |
| 2015/0235046 | A1* | 8/2015 | Takeda | H04W 4/80 726/19 |
| 2016/0042212 | A1* | 2/2016 | Hiraiwa | G06K 7/10356 235/439 |
| 2016/0321467 | A1* | 11/2016 | Keber | G06F 21/6218 |
| 2017/0337461 | A1* | 11/2017 | Jesme | G06K 19/0723 |
| 2018/0189527 | A1* | 7/2018 | Kim | G06K 7/10297 |
| 2021/0125715 | A1* | 4/2021 | Burbank | A61B 5/7475 |
| 2022/0398887 | A1* | 12/2022 | Pandey | G06K 19/0723 |

* cited by examiner

METHOD OF UNLOCKING AN OPERATION OF A DEVICE WITH A TINY RFID TAG EMBEDDED ON AN INTEGRATED CIRCUIT

BACKGROUND

The use of integrated circuits (ICs) has revolutionized the electronics industry, enabling the development of various electronic devices that are smaller, faster, and more efficient. However, the widespread adoption of ICs has also led to the rise of counterfeits, which pose a significant threat to the industry, economy, and public safety. Counterfeit ICs are often sold as genuine products but can be of lower quality and can compromise the functionality and reliability of electronic devices, leading to system failures, data breaches, and other security risks.

To combat this issue, various anti-counterfeiting measures have been implemented, including authentication through Radio-Frequency Identification (RFID) technology. RFID is a wireless communication technology that allows for the identification and tracking of objects using radio waves. An RFID system typically consists of an RFID tag and an RFID reader. The tag contains a unique identification code that can be read by an RFID reader, allowing for quick and easy authentication.

Incorporating RFID technology into ICs can significantly enhance anti-counterfeiting measures. By embedding a tiny RFID tag in an IC, the authenticity of the IC can be quickly and easily verified using an RFID reader. This will help prevent the use of counterfeit ICs in electronic devices, ensuring that they function as intended and do not pose any risks to the users.

A challenge has been making the RFID tag tiny. An approach to making embedded RFID tags tiny (less than 0.1 mm2 in area and, more specifically, less than 0.05 mm$^2$ in area) in conjunction with an IC is disclosed in K. Bhanushali, et al. "A 125 µm×245 µm Mainly Digital UHF EPC Gent Compatible RFID Tag in 55 nm CMOS Process," in IEEE Journal of Radio Frequency Identification, vol. 5, No. 3, pp. 317-323, September 2021, doi: 10.1109/JR-FID.2021.3087448, which is incorporated by reference herein in its entirety. This concept is applied in U.S. Pat. No. 11,626,206 ("Method of Unlocking Operation of a Device"), issued on Apr. 11, 2023, and U.S. Pat. No. 11,475,993, both of which are incorporated by reference herein in their entirety, and of which the present patent application is a continuation-in-part.

Therefore, there is a need for ICs with a tiny embedded RFID tag to enhance anti-counterfeiting measures in the electronics industry. And, in particular, a method to unlock an operation of a device and/or system using a tiny embedded RFID tag that authenticates the IC. The use of such ICs will provide a reliable and efficient way to authenticate electronic devices and ensure their safety and security.

BRIEF SUMMARY

Embodiments of the present disclosure may include a method of unlocking an operation of a device, the method including the steps of inserting an integrated circuit into the device, the device having a Radio Frequency Identification (RFID) reader, the device having a capability that may be in a locked state. In some embodiments, the integrated circuit having a first tiny RFID tag embedded therein, the first tiny RFID tag having an area of 0.05 mm2 or less, the first tiny RFID tag being a primarily digital tiny tag that may be implemented using portable digital IP blocks, the first tiny RFID tag utilizing dual-phase RF-only logic.

In some embodiments, power supply transistors may be shared across a chip that may include the integrated circuit and the first tiny RFID tag, and a foundry standard cell library may be used in manufacturing the first tiny RFID tag. Embodiments may also include reading data from the first tiny RFID tag. Embodiments may also include verifying that the RFID data that has been read meets criteria for unlocking the device.

Embodiments may also include after verifying the RFID data, unlocking the capability of the device for operation. In some embodiments, the method further including connecting the device to a computer network. In some embodiments, the RFID data may be encoded solely at a foundry and may be not user-programmable.

In some embodiments, the method further including encoding the first tiny RFID tag with data at the foundry. In some embodiments, the method may include the step of interacting between the device and the integrated circuit in conjunction with unlocking the operation of the device, such that at least one of the device and the integrated circuit interrogates and receives a reply from the other before the device may be unlocked.

In some embodiments, the integrated circuit may be on a card, the method further including inserting the card into the device. In some embodiments, the medical device includes the RFID reader and at least a second component that does not have an RFID reader, the RFID reader and the second component being digitally interconnected but physically spaced apart.

In some embodiments, the device employs artificial intelligence (AI) and/or machine learning, the step of unlocking the capability of the device may include unlocking an artificial intelligence and/or machine learning capability. In some embodiments, the first tiny RFID tag operates in the 860-960 MHz band. In some embodiments, the RFID reader uses an ASK modulation scheme. In some embodiments, circuit operation may be paused during low-RF periods.

Embodiments of the present disclosure may also include a method of unlocking an operation of a device, the method including the steps of inserting an integrated circuit into the device, the device having a Radio Frequency Identification (RFID) reader, the device having a capability that may be in a locked state. In some embodiments, the integrated circuit having a first tiny RFID tag embedded therein, the first tiny RFID tag having an area of 0.1 mm2 or less, the first tiny RFID tag being a primarily digital tag that may be implemented using portable digital IP blocks, the first tiny RFID tag utilizing dual-phase RF-only logic.

In some embodiments, power supply transistors may be shared across a chip that may include the integrated circuit and the first tiny RFID tag, and a foundry standard cell library may be used in manufacturing the first tiny RFID tag. Embodiments may also include reading first RFID data from the first tiny RFID tag. Embodiments may also include verifying that the first RFID data that has been read meets criteria for unlocking the device.

Embodiments may also include after verifying the first RFID data. Embodiments may also include unlocking the capability of the device for operation. In some embodiments, the method may include connecting the device to a computer network. In some embodiments, at least some of the first RFID data may be encoded solely at a foundry and may be not user-programmable.

In some embodiments, the method further including encoding the first tiny RFID tag with data at the foundry. In some embodiments, the method further including the step of at least one of a component that may include the integrated circuit and the device interrogating the other, receiving a reply from the other, and providing the other access when the reply may be acceptable.

In some embodiments, the chip may include a second tiny RFID tag that has second RFID data, the method further including reading the second RFID data from the second tiny RFID tag. In some embodiments, the second tiny RFID tag may be embedded in the integrated circuit and may be spaced apart from the first tiny RFID tag. In some embodiments, the method may include the step of verifying data from both the first and the second tiny RFID tags to unlock the device.

In some embodiments, the device may be a medical or veterinary device. In some embodiments, the integrated circuit may be on a card, the method further including inserting the card into the device. In some embodiments, the device includes a card reader that includes the RFID reader and a second component that may be digitally interconnected with card reader but may be physically spaced apart from the card reader.

In some embodiments, the device employs artificial intelligence (AI) and/or machine learning, the step of unlocking the capability of the device may include unlocking an artificial intelligence and/or machine learning capability. In some embodiments, the step of unlocking the device further includes enabling a blockchain transaction.

In some embodiments, the device has a machine vision capability. In some embodiments, the first tiny RFID tag occupies less than 10% of the area of the chip. In some embodiments, the first tiny RFID tag occupies less than 10% of the area of the chip, has a sensitivity of −2 dBm or better, and/or operates in the 860-960 MHz band.

In some embodiments, the device may be a medical and/or veterinary transcutaneous electrical nerve stimulator and the method includes the step of performing transcutaneous electrical nerve stimulation. In some embodiments, the device may be a medical and/or veterinary pulse electromagnetic field (PEMF) therapy device, and the method includes the step of performing PEMF therapy. In some embodiments, the device may be a medical and/or veterinary device that includes a laser, and the method includes performing laser therapy.

Embodiments of the present disclosure may also include a method of unlocking an operation of a device, the method including the steps of inserting an integrated circuit into the device, the device having a Radio Frequency Identification (RFID) reader, the device having a capability that may be in a locked state. In some embodiments, the integrated circuit having a first tiny RFID tag embedded therein, the first tiny RFID tag having an area of 0.1 mm2 or less, the first tiny RFID tag being a primarily digital tag that may be implemented using portable digital IP blocks, the first tiny RFID tag utilizing dual-phase RF-only logic.

In some embodiments, power supply transistors may be shared across a chip that may include the integrated circuit and the first tiny RFID tag, and a foundry standard cell library may be used in manufacturing the first tiny RFID tag. Embodiments may also include reading first RFID data from the first tiny RFID tag. Embodiments may also include verifying that the first RFID data that has been read meets criteria for unlocking the device.

Embodiments may also include after verifying the first RFID data, unlocking the capability of the device for operation. In some embodiments, the method may include connecting the device to a computer network. In some embodiments, at least some of the first RFID data may be encoded solely at a foundry and may be not user-programmable.

In some embodiments, the method further including encoding the first tiny RFID tag with data at the foundry. In some embodiments, the method further including the step of at least one of a component that may include the integrated circuit and the device interrogating the other, receiving a reply from the other, and providing the other access when the reply may be acceptable.

In some embodiments, the method may be used in conjunction with artificial intelligence (AI) for identification and authentication, fraud detection, behavioral analysis, predictive analytics, and/or access control. In some embodiments, the integrated circuit may be on a credit or debit card, the method including authorizing a credit or debit card transaction. In some embodiments, the RFID tag has an area of 0.05 mm2 or less.

In any of the foregoing embodiments, various additional steps and/or other details may be incorporated, either separately or in combination with one or more other features. Consequently, the invention is not limited to specific combinations of elements, and may be comprised of a combination of steps and/or features not specifically identified herein.

DETAILED DESCRIPTION

Figure 1:
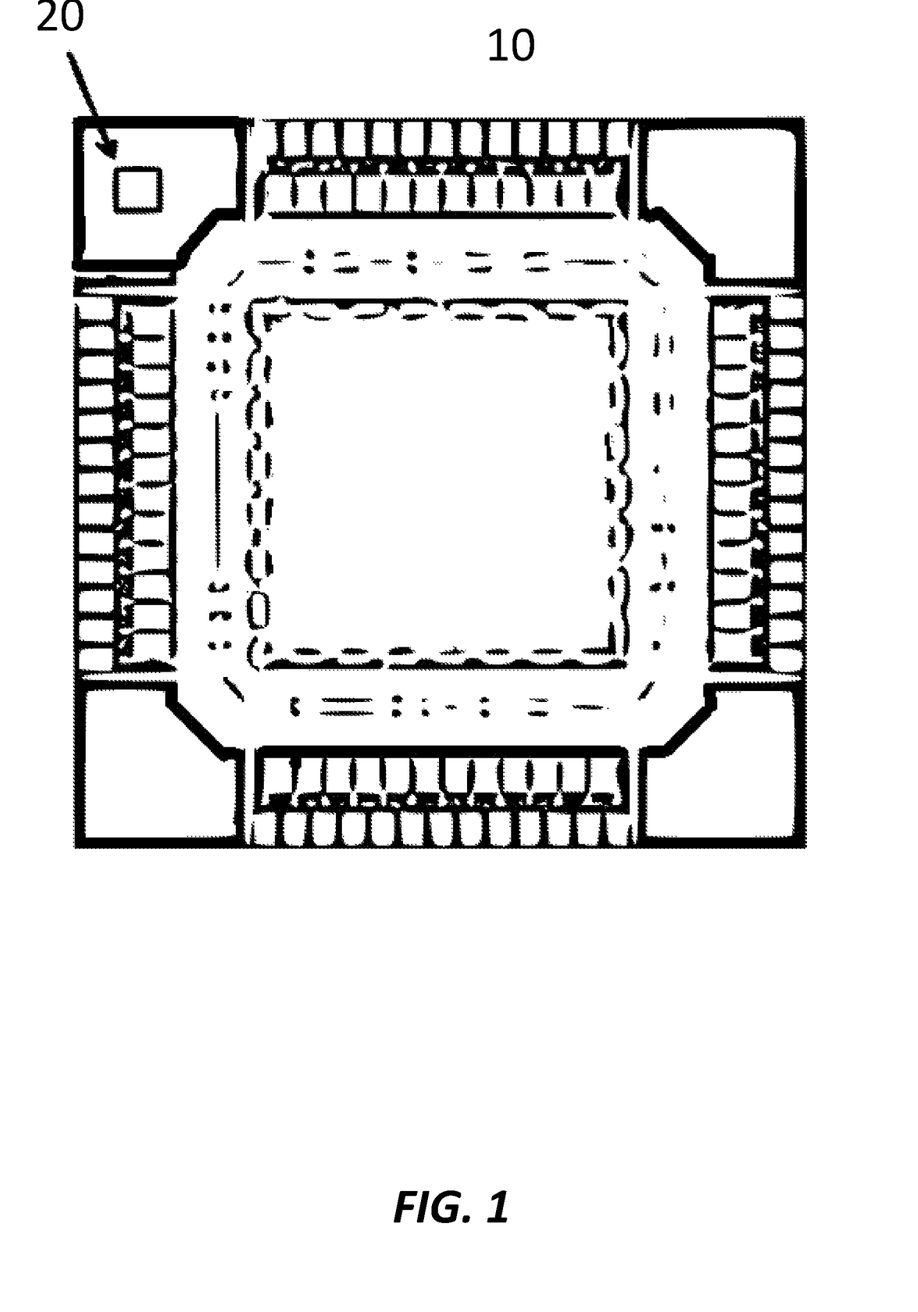
FIG. 1 is an integrated circuit chip with an RFID tag embedded in it.

FIG. 1 illustrates an integrated circuit chip 10 having an embedded RFID tag 20, the integrated circuit having a first tiny RFID tag embedded therein, the RFID tag having an area of 0.1 mm2 or less, the RFID tag being a largely digital tag that may be implemented using portable digital IP blocks, the RFID tag utilizing dual-phase RF-only logic. Power supply transistors may be shared across the integrated circuit chip and a foundry standard cell library may be used in manufacturing the tiny RFID tag. The RFID tag may optionally be encoded with data at the foundry at which it is made, and only optionally have user-programmable capacity.

Figure 2:
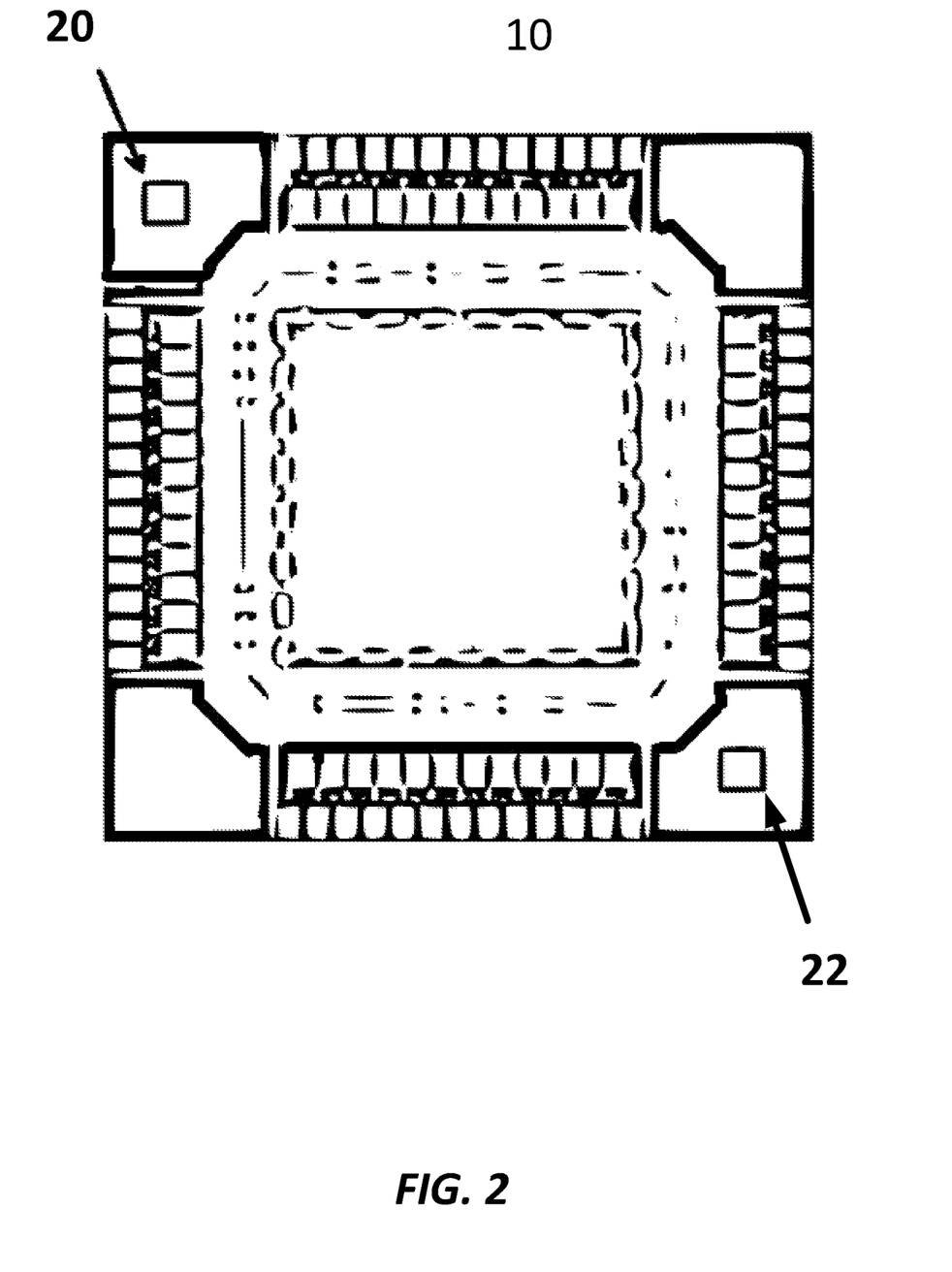
FIG. 2 is an integrated circuit chip with two RFID tags embedded in it.

FIG. 2 illustrates an integrated circuit chip 10 having a first embedded RFID tag 20, and a second embedded RFID tag 22. Consequently, FIG. 2 illustrates that in one embodiment, more than one RFID tag may be embedded in the integrated circuit chip. As a further possibility, more than two RFID tags may be embedded in the integrated circuit chip. Also, it is possible to use a second RFID tag in a system according to the present invention, in which the second RFID tag is embedded into a second integrated circuit chip, or is simply an RFID tag not embedded in chip.

Figure 3:
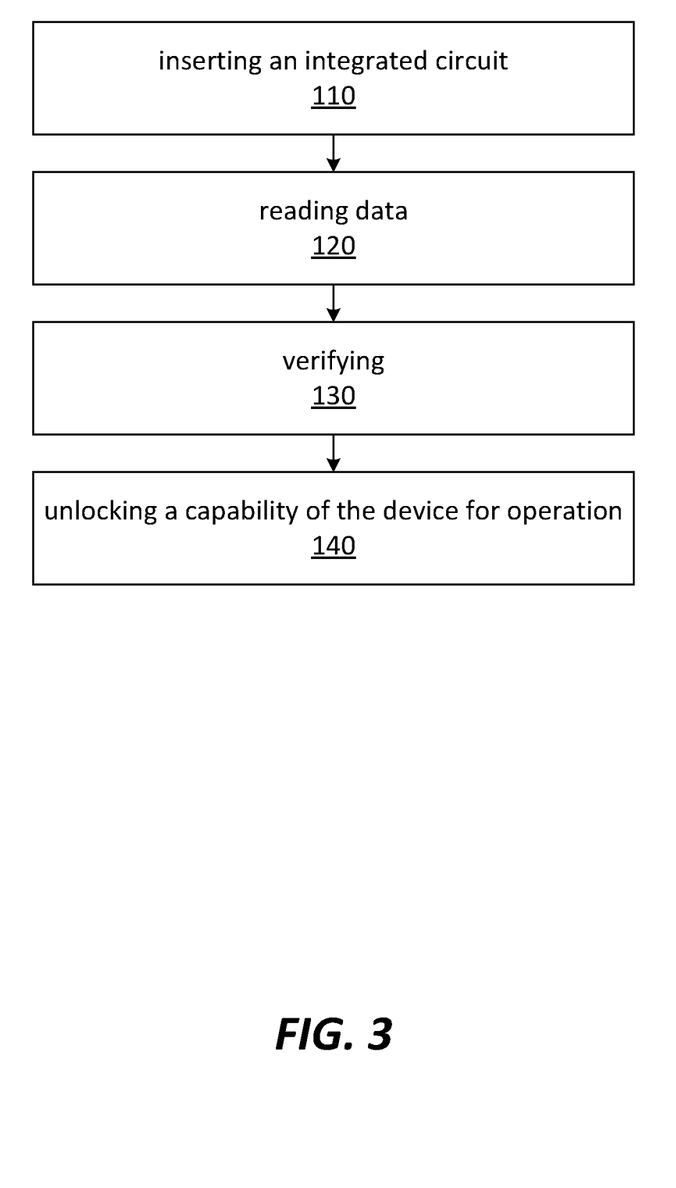
FIG. 3 is a flowchart illustrating a method of unlocking an operation of a Class III medical device, according to some embodiments of the present disclosure.
Figure 4:
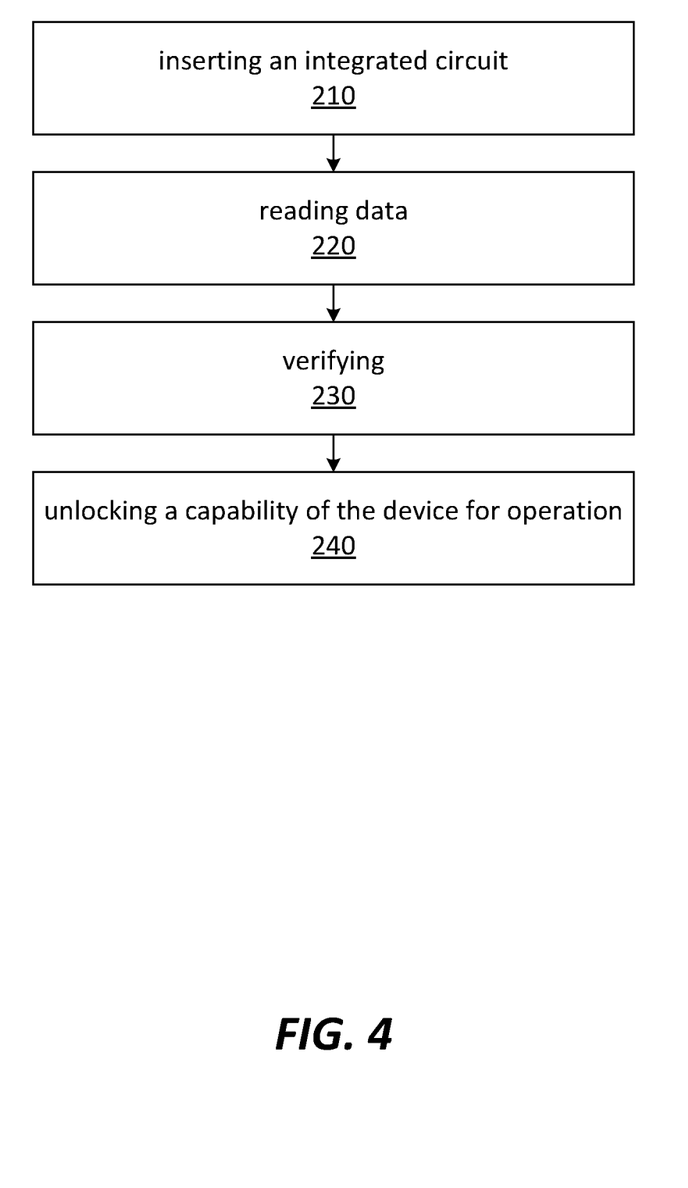
FIG. 4 is a flowchart illustrating a method of unlocking an operation of a Class III medical device, according to some embodiments of the present disclosure.
Figure 5:
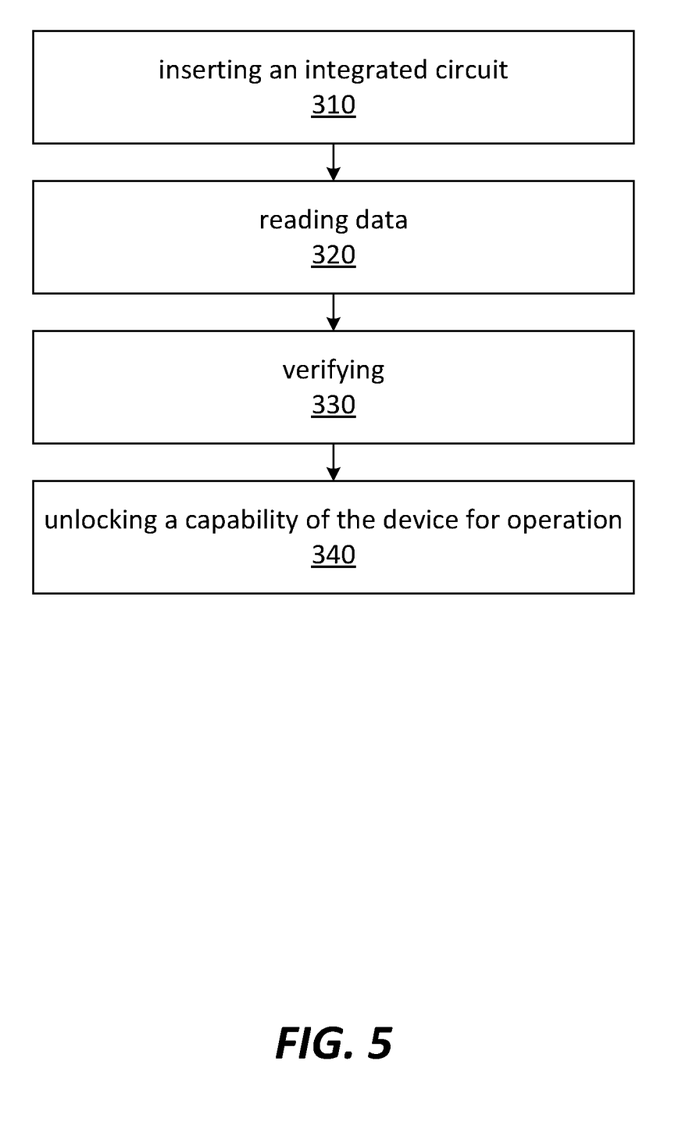
FIG. 5 is a flowchart illustrating a method of unlocking an operation of a medical device, according to some embodiments of the present disclosure.

FIG. 3 is a flowchart that shows a method of unlocking an operation of a Class III medical device, according to some embodiments of the present disclosure. At 110, the method may include inserting an integrated circuit into a medical device having an RFID reader, the medical device having a capability that may be in a locked state, the integrated circuit having a first tiny RFID tag embedded therein, the RFID tag having an area of about 0.1 mm2 or less and being largely digital utilizing RF-only logic. At 120, the method may include reading data from the first RFID tag.

At 130, the method may include verifying that the RFID data that has been read from the first RFID tag meets criteria for unlocking the device. At 140, the method may include, after verifying the RFID data from the first RFID tag, unlocking the capability of the device for operation. In some embodiments, the integrated circuit may further comprise a second embedded tiny RFID tag that may be spaced apart from the first RFID tag, the second RFID tag having an area of about 0.1 mm2 or less. the method further comprising reading data from the second RFID tag. In some embodiments, the device may be a Class III medical device as defined by the FDA, and may be suitable for use in treating COVID 19 in a human body and requires regulatory premarket approval to evaluate the safety and effectiveness of the device.

FIG. 2 is a flowchart that shows a method of unlocking an operation of a Class III medical device, according to some embodiments of the present disclosure. At 210, the method may include inserting an integrated circuit into a medical device having an RFID reader, the medical device having a capability that may be in a locked state. In some embodiments, the integrated circuit having a first tiny RFID tag embedded therein, the RFID tag having an area of 0.1 mm2 or less, the RFID tag being a largely digital tag that may be implemented using portable digital IP blocks, the RFID tag utilizing dual-phase RF-only logic.

In some embodiments, power supply transistors may be shared across an integrated circuit chip and a foundry standard cell library may be used in manufacturing the tiny RFID tag. At 220, the method may include reading data from the tiny RFID tag. At 230, the method may include verifying that the RFID data that has been read meets criteria for unlocking the device. At 240, the method may include, after verifying the RFID data, unlocking the capability of the device for operation.

In some embodiments, the device may be a Class III medical device as defined by the FDA, and may be suitable for use in treating COVID 19 in a human body and requires regulatory premarket approval to evaluate the safety and effectiveness of the device. In some embodiments, the medical device may be an oxygen delivery device, the method further comprising delivering oxygen to the body. In some embodiments, the medical device may deliver nanoparticles into a human body, the method further comprising delivering nanoparticles into the body.

In some embodiments, the medical device may assist function of a human kidney, the method further comprising assisting the function of a human kidney. In some embodiments, the medical device may be adapted to be implanted in a human body, the method further comprising implanting at least a component of the medical device into the human body. In some embodiments, the medical device may be a cardiac device, the method further comprising assisting cardiac function in a human with the cardiac device.

In some embodiments, the medical device may be an implantable prosthesis, the method further comprising the step of implanting the implantable prosthesis into a human. In some embodiments, the medical device may be an internet of things (IOT) device, the method further comprising connecting the device to a computer network. In some embodiments, the RFID data may include data sufficient to identify a uniform resource locator (URL).

In some embodiments, the RFID data may be encoded solely at a foundry and may be not user-programmable. In some embodiments, the method further comprising encoding the RFID tag with data at a foundry. In some embodiments, the step of unlocking the device may further include enabling a blockchain transaction. In some embodiments, the step of unlocking the device may further include enabling a cryptocurrency transaction.

In some embodiments, the cryptocurrency transaction may be to pay for a medical procedure. In some embodiments, one of the integrated circuit and the device may have a non-fungible token (NFT) associated with it. In some embodiments, the RFID data may include an identifier correlating the non-fungible token (NFT) with the integrated circuit or device. In some embodiments, the integrated circuit may be on a card, the method further comprising inserting the card into the device.

In some embodiments, the device may include an RFID reader and at least a second component that may be not an RFID reader, the RFID reader and the second component being digitally interconnected but physically spaced apart. In some embodiments, the medical device may employ artificial intelligence (AI) and/or machine learning, the step of unlocking a capability of the device comprises unlocking an artificial intelligence and/or machine learning capability.

In some embodiments, the medical device may have a machine vision capability, the step of unlocking a capability of the device comprises unlocking a machine vision capability. In some embodiments, the RFID tag may have a sensitivity of −2 dBm or better. In some embodiments, the RFID tag may operate in the 860-960 MHz band. In some embodiments, the RFID reader may use an ASK modulation scheme. In some embodiments, circuit operation may be paused during low-RF periods.

In some embodiments, the integrated circuit may be part of at least one of a hard disk drive (HDD), a solid state drive (SSD), and flash memory card. In some embodiments, the integrated circuit may be part of a biometric authentication device. In some embodiments, the step of interacting between the medical device and the integrated circuit after the RFID data may be verified. In some embodiments, the integrated circuit may comprise a second RFID tag, the method further comprising reading data from the second RFID tag.

In some embodiments, the second RFID tag may be imbedded in the integrated circuit, has an area of 0.1 mm2 or less, and may be spaced apart from the first RFID tag. In some embodiments, the method further comprises the step of verifying data from both the first and the second RFID tag to unlock the device. In some embodiments, the integrated circuit may be part of a component, and the method further comprises the step of the component interrogating the medical or other device, receiving a reply from the device, and providing the device access to an aspect of the component when the reply may be acceptable. Similarly, alternatively the medical or other device or system may interrogate the component and receive a reply from the component, as a step in unlocking a capability of the device or system. For example, the device or system may interrogate the component and may require an appropriate reply from the component before the capability of the device or system is unlocked.

In some embodiments, the step of unlocking comprises enabling transmission of at least one of video and audio. In some embodiments, the embedded RFID tag may be part of a hospital patient bracelet. In some embodiments, the hospital patient bracelet may include writable memory, the method further comprising the step of reading data from the memory and writing new data to the memory.

FIG. 3 is a flowchart that shows a method of unlocking an operation of a medical device, according to some embodiments of the present disclosure. At 310, the method may include inserting an integrated circuit into a medical device having an RFID reader, the medical device having a capability that may be in a locked state, the integrated circuit having a first tiny RFID tag embedded therein, the embedded RFID tag having an area of 0.1 mm2 or less. At 320, the method may include reading data from the tiny RFID tag. At 330, the method may include verifying that the RFID data that has been read meets criteria for unlocking the device.

At 340, the method may include, after verifying the RFID data, unlocking the capability of the device for operation. In some embodiments, the medical further comprises implanting the device into an animal in a veterinary setting. In some embodiments, the step of implanting the device into an animal in a veterinary setting comprises transvenous pacemaker implantation. In some embodiments, the step of implanting the device into an animal in a veterinary setting comprises implanting a prosthetic device.

Concerning the locking/unlocking function, one approach is a software-controlled system, in which the software maintains the system in a locked configuration unless a condition is satisfied. For example, the software only unlocks a capability of the device when data read from the RFID tag satisfies a criteria. Alternatively, electro-mechanical and/or mechanical locking systems may be employed.

More generally, an integrated circuit with a tiny RFID tag embedded in it, which unlocks the capability of a device or system only if the data on the RFID tag matches predefined criteria, has potential applications in various fields where security and access control are crucial. Some applications are:

Secure access control: Use in access control systems for secure facilities, such as military bases, research laboratories, or corporate offices, to ensure that only authorized personnel can access the facility.

Electronic locks: Use in electronic locks, such as those used in hotel rooms or private residences, to provide an added layer of security and prevent unauthorized access.

Asset tracking: Use in asset tracking systems, such as those used in warehouses or shipping facilities, to ensure that only authorized personnel can access valuable or sensitive assets.

Healthcare: Use in healthcare applications, such as patient data management systems, to ensure that only authorized healthcare professionals can access sensitive patient information.

Transportation: Use in transportation systems, such as public transportation, to ensure that only authorized personnel can operate the vehicle or access restricted areas.

Manufacturing: Use in manufacturing systems, such as automated production lines, to ensure that only authorized personnel can access and operate the equipment.

Financial Transactions: Use in authorizing financial transactions, which may include consumer purchases at stores. For example, the user may present a card to a card reader that includes an RFID reader. Only if data encoded on the RFID tag is correct will a financial transaction be authorized, optionally in conjunction with other steps such as interrogating the card.

Credit and Other Types of Cards: When a credit card has an integrated circuit and a tiny RFID tag, the system can use both technologies to authorize a transaction. One approach is as follows, with variations possible:

The cardholder holds the credit card near an RFID reader at the point of sale terminal. The RFID reader sends out a radio frequency signal, which activates the RFD tag on the credit card.

The RFID tag on the credit card contains encrypted information, including the card number, expiration date, and security code, which is transmitted back to the RFID reader.

The RFID reader sends the encrypted information from the RFID tag to the payment processor, which verifies the information and authorizes the transaction.

At the same time, the cardholder inserts the credit card into a card reader or terminal. The terminal sends a signal to the credit card, activating the integrated circuit.

The integrated circuit on the credit card communicates with the terminal to establish a secure connection, using a process called mutual authentication to ensure that the terminal is authorized to process the transaction and that the credit card is a legitimate card.

Once the connection is established, the terminal sends a request for payment authorization to the credit card's integrated circuit.

The integrated circuit on the credit card checks the account status, available credit limit, and other relevant information to determine whether the transaction can be authorized.

If the transaction is authorized, the integrated circuit on the credit card generates an encrypted message that contains the authorization data, such as the transaction amount and a unique transaction code.

The encrypted message is sent back to the terminal, which decrypts the message and processes the transaction.

Using both the integrated circuit and the tiny RFID tag adds an extra layer of security and convenience to credit card transactions. The tiny RFID tag allows for faster and easier contactless payments, while the integrated circuit provides secure communication and authorization for the transaction. This concept can be extended to various other types of cards that play a role in authorizing something.

Authentication Card in Conjunction with Artificial Intelligence and/or Machine Learning: An authentication card with an integrated circuit and a tiny RFID tag encoded with authentication data can be used in conjunction with artificial intelligence (AI) or machine learning (ML) in a variety of ways, including, as examples only:

Identification and authentication: An AI system can use the RFID tag encoded with authentication data to quickly identify and authenticate individuals. The system can compare the authentication data with a database of authorized users to determine if the person is authorized to access a particular system, device or location.

Fraud detection: AI or ML algorithms can be trained to analyze transaction data, including data from the authentication card, to detect patterns that may indicate fraudulent activity. For example, the system may flag transactions where the authentication card was used in an unusual location or at an unusual time. Behavioral analysis: AI or ML algorithms can be used to analyze patterns of behavior associated with the use of the authentication card. By analyzing this data, the system can identify unusual behavior that may indicate fraud or security breaches.

Predictive analytics: By combining data from the authentication card with other sources of data, such as transaction histories and user profiles, AI or ML algorithms can be used to predict future behavior or outcomes. For example, the system may predict which users are more likely to commit fraud or which transactions are more likely to be fraudulent.

Access control: An AI system can use data from the authentication card to control access to specific areas or devices. The system can be programmed to only allow authorized users with the proper authentication card to access specific areas or devices.

Embodiments of the present invention may be used in conjunction with specific applications for RFID technology that are identified in U.S. patent application Ser. No. 11/056,554 filed by Scott R. Hansen and published as US Patent Publication US20060180647A1, entitled "RFID Applications" and which is incorporated by reference herein in its entirety. Applications identified in that patent application may incorporate an RFID tag having an area of 0.1 mm$^2$ or less, or 0.05 mm$^2$ or less, in conjunction with an integrated as described. This includes, for example, adhesive labels that incorporate the RFID/IC combination described herein, as well as tags, labels, and other mechanisms.

Figure 6:
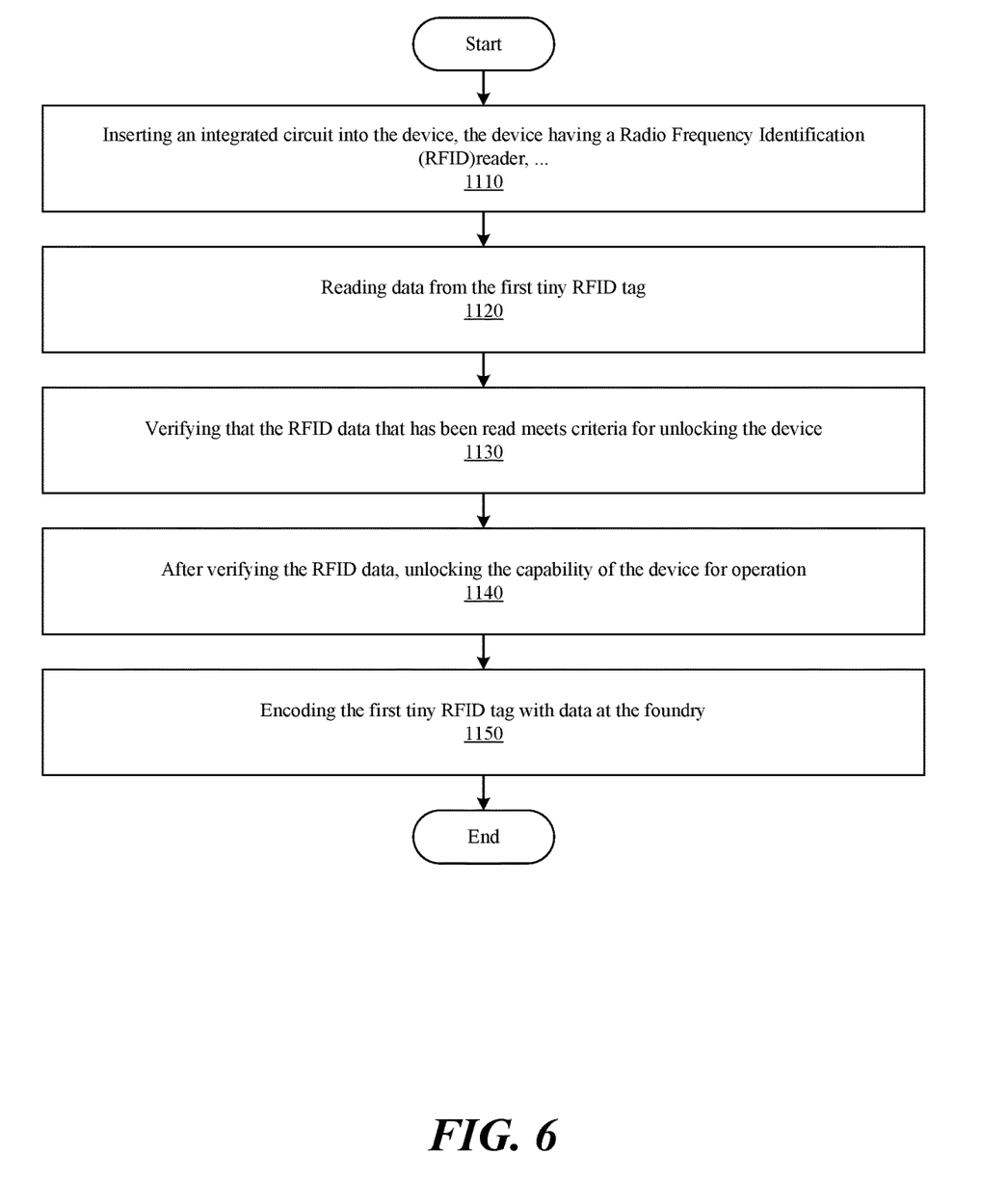
FIG. 6 is a flowchart illustrating a method of unlocking an operation of a device, according to some embodiments of the present disclosure.

Returning now to the drawings, FIG. 6 is a flowchart that describes a method of unlocking an operation of a device, according to some embodiments of the present disclosure. In some embodiments, at 1110, the method may include inserting an integrated circuit into the device, the device having a Radio Frequency Identification (RFID) reader, the device having a capability that may be in a locked state. At 1120, the method may include reading data from the first tiny RFID tag. At 1130, the method may include verifying that the RFID data that has been read meets criteria for unlocking the device. At 1140, the method may include, after verifying the RFID data, unlocking the capability of the device for operation. At 1150, the method may include encoding the first tiny RFID tag with data at the foundry.

In some embodiments, the steps of, the method may include 1110 to 1150. The integrated circuit having a first tiny RFID tag embedded therein, the first tiny RFID tag having an area of 0.05 mm2 or less, the first tiny RFID tag being a primarily digital tiny tag that may be implemented using portable digital IP blocks, the first tiny RFID tag utilizing dual-phase RF-only logic. Power supply transistors may be shared across a chip that comprises the integrated circuit and the first tiny RFID tag, and a foundry standard cell library may be used in manufacturing the first tiny RFID tag.

In some embodiments, the method further comprising connecting the device to a computer network. The RFID data may be encoded solely at a foundry and may be not user-programmable. The method. The method further comprises the step of interacting between the device and the integrated circuit in conjunction with unlocking the operation of the device, such that at least one of the device and the integrated circuit interrogates and receives a reply from the other before the device may be unlocked.

In some embodiments, the integrated circuit may be on a card. The method may include inserting the card into the device. In some embodiments, the medical device may include the RFID reader and at least a second component that does not have an RFID reader, the RFID reader and the second component being digitally interconnected but physically spaced apart. In some embodiments, the device may employ artificial intelligence (AI) and/or machine learning, the step of unlocking the capability of the device comprises unlocking an artificial intelligence and/or machine learning capability. In some embodiments, the first tiny RFID tag may operate in the 860-960 MHz band. In some embodiments, the RFID reader may use an ASK modulation scheme. Circuit operation may be paused during low-RF periods.

Figure 7A:
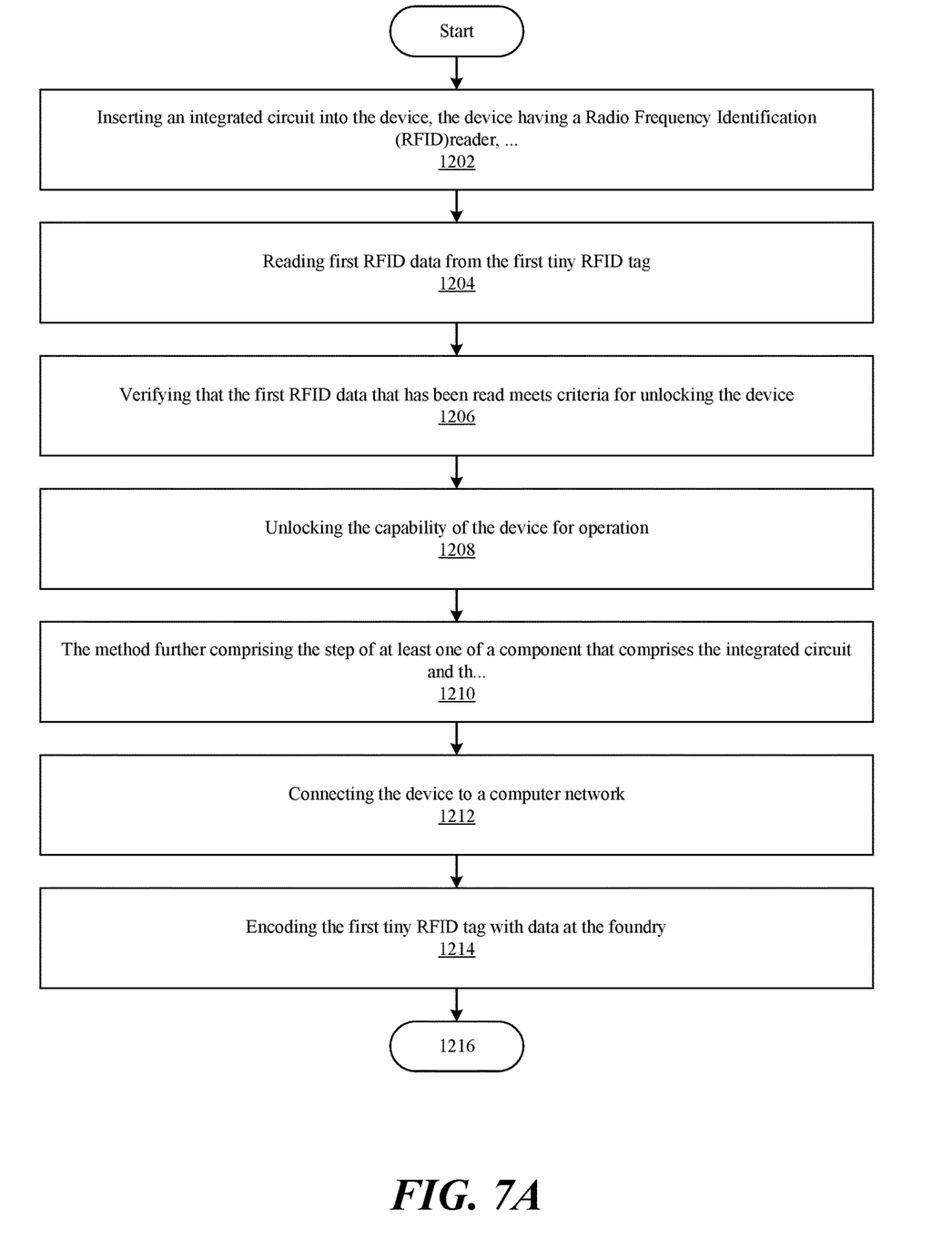
FIG. 7A is a flowchart illustrating a method of unlocking an operation of a device, according to some embodiments of the present disclosure.
Figure 7B:
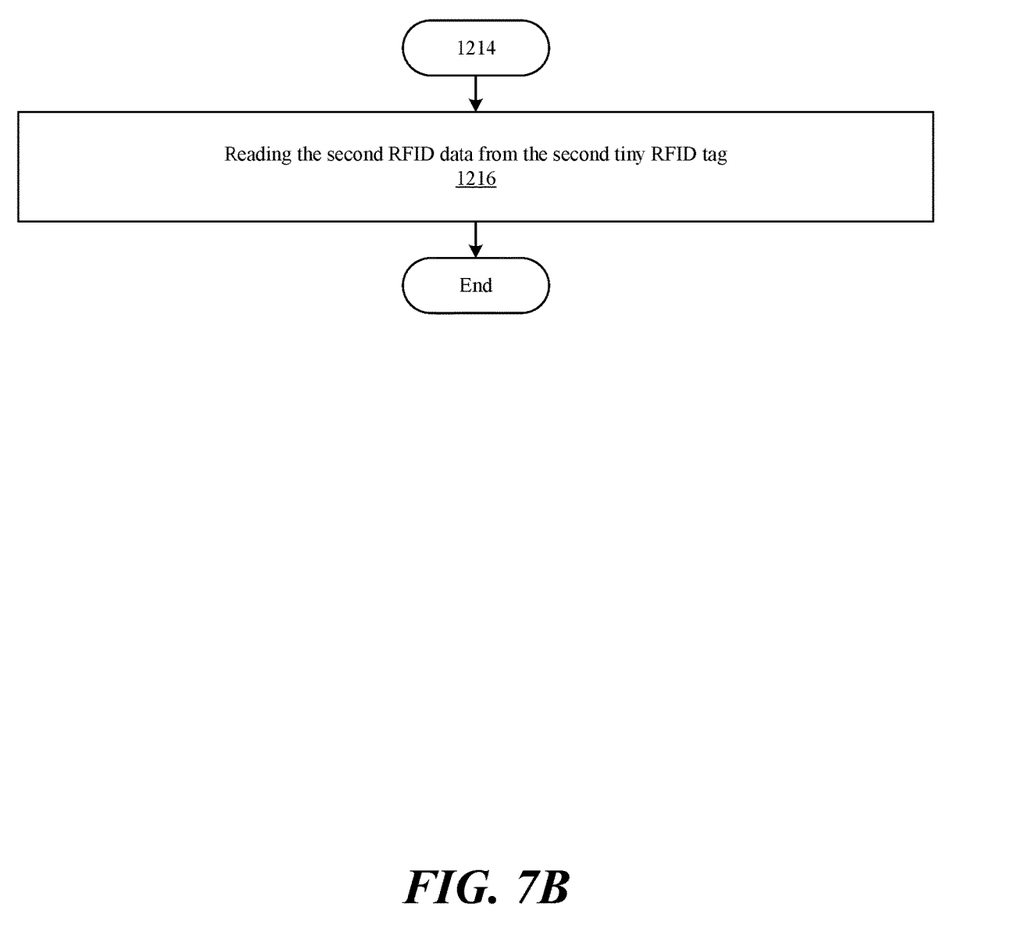
FIG. 7B is a flowchart extending from FIG. 2A and further illustrating the method of unlocking an operation of a device, according to some embodiments of the present disclosure.

FIGS. 7A to 7B are flowcharts that describe a method of unlocking an operation of a device, according to some embodiments of the present disclosure. In some embodiments, at 1202, the method may include inserting an integrated circuit into the device, the device having a Radio Frequency Identification (RFID) reader, the device having a capability that may be in a locked state. At 1204, the method may include reading first RFID data from the first tiny RFID tag. At 1206, the method may include verifying that the first RFID data that has been read meets criteria for unlocking the device.

In some embodiments, at 1208, the method may include unlocking the capability of the device for operation. At 1212, the method may include connecting the device to a computer network. At 1214, the method may include encoding the first tiny RFID tag with data at the foundry. At 1210, the method may include, the method further comprising the step of at least one of a component that comprises the integrated circuit and the device interrogating the other, receiving a reply from the other, and providing the other access when the reply may be acceptable. At 1216, the method may include reading the second RFID data from the second tiny RFID tag.

In some embodiments, the steps of, the method may include 1202 to 1216. The integrated circuit having a first tiny RFID tag embedded therein, the first tiny RFID tag having an area of 0.1 mm2 or less, the first tiny RFID tag being a primarily digital tag that may be implemented using portable digital IP blocks, the first tiny RFID tag utilizing dual-phase RF-only logic. Power supply transistors may be shared across a chip that comprises the integrated circuit and the first tiny RFID tag, and a foundry standard cell library may be used in manufacturing the first tiny RFID tag.

In some embodiments, after verifying the first RFID data. The method. At least some of the first RFID data may be encoded solely at a foundry and may be not user-programmable. The second tiny RFID tag may be embedded in the integrated circuit and may be spaced apart from the first tiny RFID tag. The step of verifying data from both the first and the second tiny RFID tags to unlock the device.

In some embodiments, the device may be a medical or veterinary device. In some embodiments, the integrated circuit may be on a card. The method may include inserting the card into the device. In some embodiments, the device may include a card reader that includes the RFID reader and a second component that may be digitally interconnected with card reader but may be physically spaced apart from the card reader.

In some embodiments, the device may employ artificial intelligence (AI) and/or machine learning, the step of unlocking the capability of the device comprises unlocking an artificial intelligence and/or machine learning capability. In some embodiments, the step of unlocking the device may further include enabling a blockchain transaction. In some embodiments, the device may have a machine vision capability.

In some embodiments, the first tiny RFID tag may occupy less than 10% of the area of the chip. In some embodiments, the first tiny RFID tag may occupy less than 10% of the area of the chip, has a sensitivity of −2 dBm or better, and/or operates in the 860-960 MHz band. In some embodiments, the device may be a medical and/or veterinary transcutaneous electrical nerve stimulator. The step of performing transcutaneous electrical nerve stimulation. In some embodiments, the device may be a medical and/or veterinary pulse electromagnetic field (PEMF) therapy device. The step of performing PEMF therapy. In some embodiments, the device may be a medical and/or veterinary device that. A laser. The method may include performing laser therapy.

Figure 8:
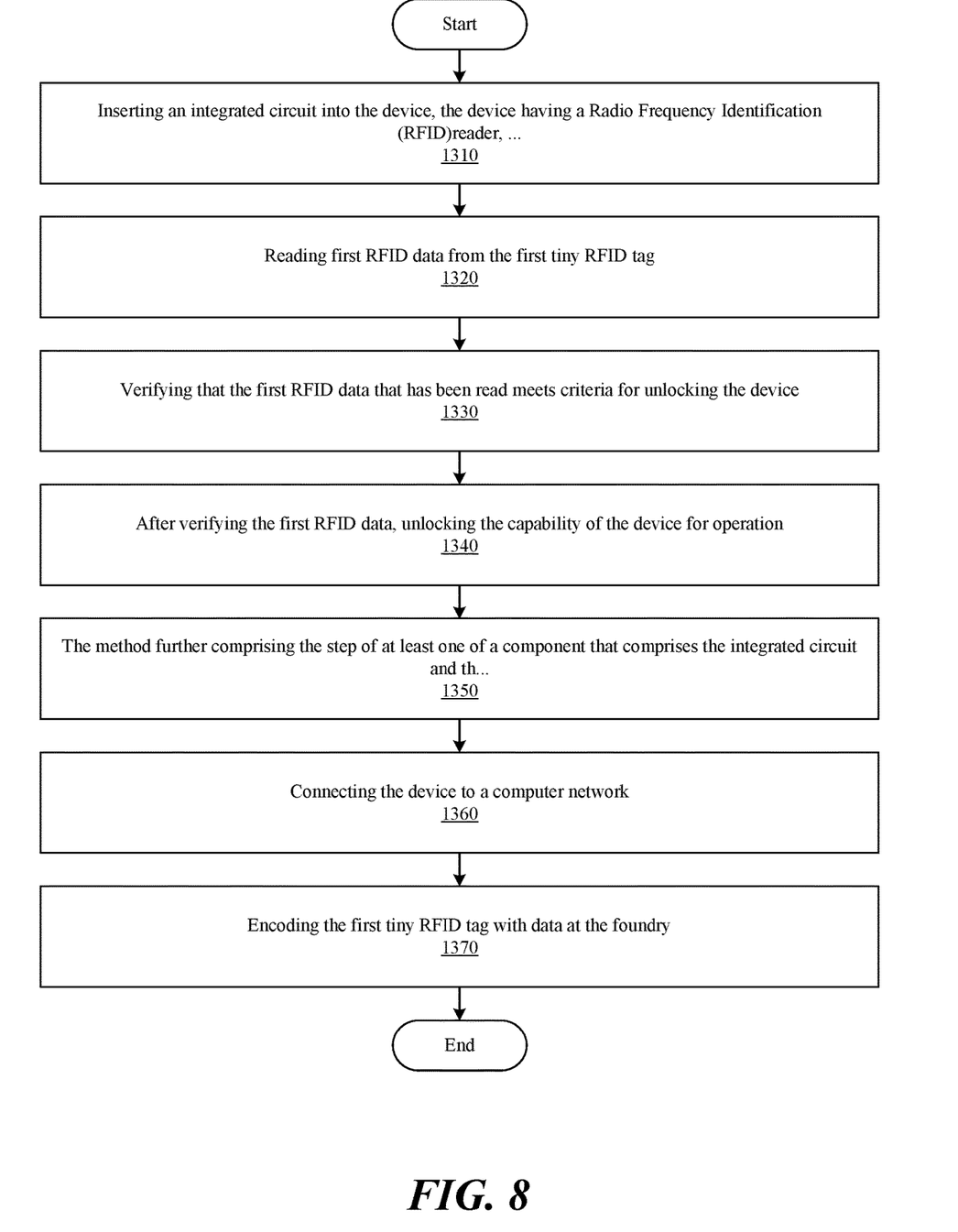
FIG. 8 is a flowchart illustrating a method of unlocking an operation of a device, according to some embodiments of the present disclosure.

FIG. 8 is a flowchart that describes a method of unlocking an operation of a device, according to some embodiments of the present disclosure. In some embodiments, at 1310, the method may include inserting an integrated circuit into the device, the device having a Radio Frequency Identification (RFID) reader, the device having a capability that may be in a locked state. At 1320, the method may include reading first RFID data from the first tiny RFID tag. At 1330, the method may include verifying that the first RFID data that has been read meets criteria for unlocking the device.

In some embodiments, at 1340, the method may include, after verifying the first RFID data, unlocking the capability of the device for operation. At 1360, the method may include connecting the device to a computer network. At 1370, the method may include encoding the first tiny RFID tag with data at the foundry. At 1350, the method may include, the method further comprising the step of at least one of a component that comprises the integrated circuit and the device interrogating the other, receiving a reply from the other, and providing the other access when the reply may be acceptable.

In some embodiments, the steps of, the method may include 1310 to 1350. The integrated circuit having a first tiny RFID tag embedded therein, the first tiny RFID tag having an area of 0.1 mm2 or less, the first tiny RFID tag being a primarily digital tag that may be implemented using portable digital IP blocks, the first tiny RFID tag utilizing dual-phase RF-only logic. Power supply transistors may be shared across a chip that comprises the integrated circuit and the first tiny RFID tag, and a foundry standard cell library may be used in manufacturing the first tiny RFID tag. The method. At least some of the first RFID data may be encoded solely at a foundry and may be not user-programmable.

In some embodiments, the method may be used in conjunction with artificial intelligence (AI) for identification and authentication, fraud detection, behavioral analysis, predictive analytics, and/or access control. In some embodiments, the integrated circuit may be on a credit or debit card. The method may include authorizing a credit or debit card transaction. In some embodiments, the RFID tag may have an area of 0.05 mm2 or less.

It is assumed in the foregoing that various optional features are, standing alone and in isolation from the claimed combination of elements, known in the art. For example, it is known in the art how blockchain transactions are done, how cryptocurrency can be used to purchase goods or services, and the like.

Various optional and/or additional aspects may be incorporated into embodiments of the invention, and other variations are possible. Consequently, the foregoing is presented by way of example and not limitation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method of unlocking an operation of a device, the method comprising:
   presenting an integrated circuit to the device, the device having a Radio Frequency Identification (RFID) reader, the device having a capability that is in a locked state;
   the integrated circuit having a first tiny RFID tag embedded therein, the first tiny RFID tag having an area of 0.05 mm$^2$ or less, the first tiny RFID tag being a primarily digital tiny tag that is implemented using portable digital IP blocks, the first tiny RFID tag utilizing dual-phase RF-only logic;
   wherein power supply transistors are shared across a chip that comprises the integrated circuit and the first tiny RFID tag, and a foundry standard cell library is used in manufacturing the first tiny RFID tag;
   reading RFID data, by the RFID reader, from the first tiny RFID tag;
   verifying that the RFID data that has been read meets criteria for unlocking the device; and
   after verifying the RFID data, unlocking the capability of the device for operation;
   the method further comprising connecting the device to a computer network;
   the RFID data is encoded solely at a foundry and is not user-programmable, wherein the method further comprising encoding the first tiny RFID tag with the RFID data at the foundry;
   the method further comprises interacting between the device and the integrated circuit in conjunction with unlocking the operation of the device, such that at least one of the device and the integrated circuit interrogates and receives a reply from the other before the device is unlocked.

2. The method of claim 1, in which the integrated circuit is on a card, the method further comprising inserting the card into the device.

3. The method of claim 1, in which the device includes the RFID reader and at least a second component that does not have an RFID reader, the RFID reader and the second component being digitally interconnected but physically spaced apart.

4. The method of claim 1, in which the device employs artificial intelligence (AI) and/or machine learning, the unlocking the capability of the device comprises unlocking an artificial intelligence and/or machine learning capability.

5. The method of claim 1, wherein the first tiny RFID tag operates in the 860-960 MHz band.

6. The method of claim 1, wherein the RFID reader uses an ASK modulation scheme in which circuit operation is paused during low-RF periods.

7. A method of unlocking an operation of a device, the method comprising:
introducing an integrated circuit to the device, the device having a Radio Frequency Identification (RFID) reader, the device having a capability that is in a locked state; the integrated circuit having a first tiny RFID tag embedded therein, the first tiny RFID tag having an area of 0.1 mm$^2$ or less, the first tiny RFID tag being a primarily digital tag that is implemented using portable digital IP blocks, the first tiny RFID tag utilizing dual-phase RF-only logic;
wherein power supply transistors are shared across a chip that comprises the integrated circuit and the first tiny RFID tag, and a foundry standard cell library is used in manufacturing the first tiny RFID tag;
reading first RFID data, by the RFID reader, from the first tiny RFID tag;
verifying that the first RFID data that has been read meets criteria for unlocking the device; and
after verifying the first RFID data, unlocking the capability of the device for operation;
in which the method further comprises connecting the device to a computer network;
in which at least some of the first RFID data is encoded solely at a foundry and is not user-programmable, wherein the method further comprising encoding the first tiny RFID tag with the first RFID data at the foundry;
the method further comprising at least one of a component that comprises the integrated circuit and the device interrogating the other, receiving a reply from the other, and
providing the other access when the reply is acceptable;
wherein the chip comprises a second tiny RFID tag that has second RFID data, the method further comprising reading the second RFID data from the second tiny RFID tag;
wherein the second tiny RFID tag is embedded in the integrated circuit and is spaced apart from the first tiny RFID tag; and
wherein the method further comprises the step of verifying the first RFID data from the first tiny RFID tag and the second RFID data from the second tiny RFID tag to unlock the device.

8. The method of claim 7, wherein the device is a medical or veterinary device.

9. The method of claim 7, in which the integrated circuit is on a card, the method further comprising inserting the card into the device.

10. The method of claim 7, in which the device includes a card reader that includes the RFID reader and a second component that is digitally interconnected with card reader but is physically spaced apart from the card reader.

11. The method of claim 7, in which the device employs artificial intelligence (AI) and/or machine learning, the unlocking the capability of the device comprises unlocking an artificial intelligence and/or machine learning capability.

12. The method of claim 7, wherein the unlocking the device further includes enabling a blockchain transaction.

13. The method of claim 7, wherein the device has a machine vision capability.

14. The method of claim 7, wherein the first tiny RFID tag occupies less than 10% of the area of the chip.

15. The method of claim 7, wherein the first tiny RFID tag occupies less than 10% of the area of the chip, has a sensitivity of −2 dBm or better, and/or operates in the 860-960 MHz band.

16. The method of claim 7, wherein the device is a medical and/or veterinary transcutaneous electrical nerve stimulator and the method includes performing transcutaneous electrical nerve stimulation.

17. The method of claim 7, wherein the device is a medical and/or veterinary pulse electromagnetic field (PEMF) therapy device, and the method includes performing PEMF therapy.

18. The method of claim 7, wherein the device is a medical and/or veterinary device that includes a laser, and the method includes performing laser therapy.

19. A method of unlocking an operation of a device, the method comprising:
introducing an integrated circuit to the device, the device having a Radio Frequency Identification (RFID) reader, the device having a capability that is in a locked state;
the integrated circuit having a first tiny RFID tag embedded therein, the first tiny RFID tag having an area of 0.1 mm$^2$ or less, the first tiny RFID tag being a primarily digital tag that is implemented using portable digital IP blocks, the first tiny RFID tag utilizing dual-phase RF-only logic;
wherein power supply transistors are shared across a chip that comprises the integrated circuit and the first tiny RFID tag, and a foundry standard cell library is used in manufacturing the first tiny RFID tag;
reading first RFID data, by the RFID reader, from the first tiny RFID tag;
verifying that the first RFID data that has been read meets criteria for unlocking the device; and
after verifying the first RFID data, unlocking the capability of the device for operation;
in which the method further comprises connecting the device to a computer network;
in which at least some of the first RFID data is encoded solely at a foundry and is not user-programmable, wherein the method further comprising encoding the first tiny RFID tag with data at the foundry;
the method further comprising at least one of a component that comprises the integrated circuit and the device interrogating the other, receiving a reply from the other, and providing the other access when the reply is acceptable.

20. The method of claim 19, wherein the method is used in conjunction with an artificial intelligence (AI) capability, identification and authentication, fraud detection, behavioral analysis, predictive analytics, and/or access control.

21. The method of claim 19, wherein the integrated circuit is on a credit or debit card, the method comprising authorizing a credit or debit card transaction.

22. The method of claim 19, wherein the first tiny RFID tag has an area of 0.05 mm$^2$ or less.

23. The method of claim 19, wherein the first tiny RFID tag and integrated circuit are incorporated into a label.

24. The method of claim 23, wherein the label is secured to a good for sale.

25. The method of claim 19, wherein the first tiny RFID tag occupies less than 10% of the area of the chip.

26. The method of claim 19, wherein unlocking the capability of the device further includes enabling a blockchain transaction.

27. The method of claim 19, wherein the first tiny RFID tag occupies less than 10% of the area of the chip, has a sensitivity of −2 dBm or better, and/or operates in the 860-960 MHz band.

28. The method of claim 19, wherein the first tiny RFID tag has an area of 0.05 mm$^2$ or less and occupies less than 10% of the area of the chip.

\* \* \* \* \*